United States Patent [19]

Tomita et al.

[11] 4,287,424
[45] Sep. 1, 1981

[54] SCANNING DEVICE FOR USE IN AXIAL TRANSVERSE TOMOGRAPHIC APPARATUS

[75] Inventors: Chuji Tomita; Hiroshi Abe; Katashi Shimazu, all of Kashiwa, Japan

[73] Assignee: Hitachi Medical Corporation, Tokyo, Japan

[21] Appl. No.: 96,430

[22] Filed: Nov. 21, 1979

[30] Foreign Application Priority Data

Nov. 24, 1978 [JP] Japan .......................... 53-160676[U]

[51] Int. Cl.³ ...................... G03B 41/16; G01N 21/00
[52] U.S. Cl. ................................ 250/445 T; 250/446
[58] Field of Search ............... 250/445 T, 445 R, 446, 250/447, 490

[56] References Cited
U.S. PATENT DOCUMENTS 4,104,527  8/1978  Tomita et al. .................. 250/445 T
4,187,429  2/1980  Tomita et al. .................. 250/445 T Primary Examiner—Bruce C. Anderson
Attorney, Agent, or Firm—Gerald J. Ferguson, Jr.; Joseph J. Baker

[57] ABSTRACT

A scanning device for use in axial transverse tomographic apparatus, arranged so that a support which carries thereon an X-ray source and its associated detector is mounted on a rotary disk for reciprocating linear movements, and that this rotary disk is caused to rotate through a certain angle at a time for each change of direction of the linear movements of the support. The support is moved at a plurality of different speeds. Either a single or a plurality of damping means are arranged so as to reduce the speed of movement of the support and then to accelerate this speed in association with the movement speed thereof at any changing of direction of movement of this support.

4 Claims, 9 Drawing Figures

SCANNING DEVICE FOR USE IN AXIAL TRANSVERSE TOMOGRAPHIC APPARATUS

BACKGROUND OF THE INVENTION (a) Field of the Invention

The present invention concerns a scanning device for use in axial transverse tomographic apparatus.

(b) Description of the Prior Art

In an apparatus for performing axial transverse tomography, the scanning device equipped therein is arranged so that an X-ray source and its associated detector which are arranged to oppose each other with a subject for examination intervening therebetween are caused to make linear movement along a cross section of the subject, and that said X-ray source and said detector are caused to make limited revolutions through a predetermined angle for each linear movement thereof. Such axial transverse tomography having the scanning device described above has been used widely. The scanning device is arranged so that a support to which the X-ray source and the detector are secured is provided on a rotary member for allowing a linear movement of the support, so as to be operative in such way that, for each forward movement or backward movement of the support, the rotary member is caused to make limited revolutions through a certain angle at a time. Such scanning device, however, is entailed by the problem that, because of the difficulty of substantially increasing the speed of movement of the support, the time of examination or tomography tends to become prolonged as compared with other scanning devices.

SUMMARY OF THE INVENTION

It is, therefore, a principal object of the present invention to provide a scanning device allowing the support which carries thereon an X-ray source and a detector to make linear movements at a speed higher than that of known such devices.

Another object of the present invention is to provide a scanning device of the type described above, which allows the support to make a change in the direction of its movement smoothly and quietly.

These as well as other objects of the present invention will become apparent from the following detailed description of the present invention when taken in conjunction with the accompanying drawings.

DETAILED DESCRIPTION OF THE PREFERRED EMBODIMENTS

Figure 1:
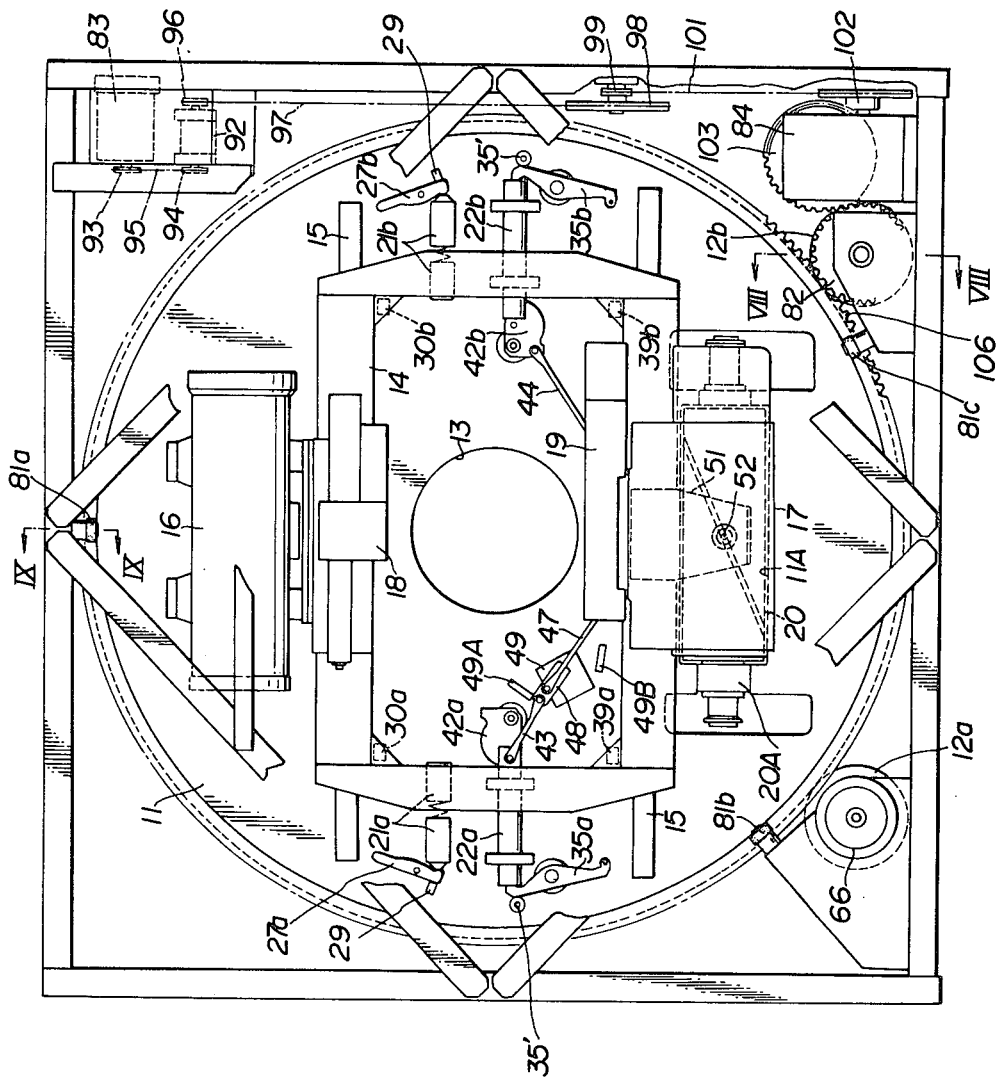
FIG. 1 is a diagrammatic front view, with parts broken away, showing an embodiment of the scanning device of the present invention for use in an axial transverse tomographic apparatus.
Figure 2:
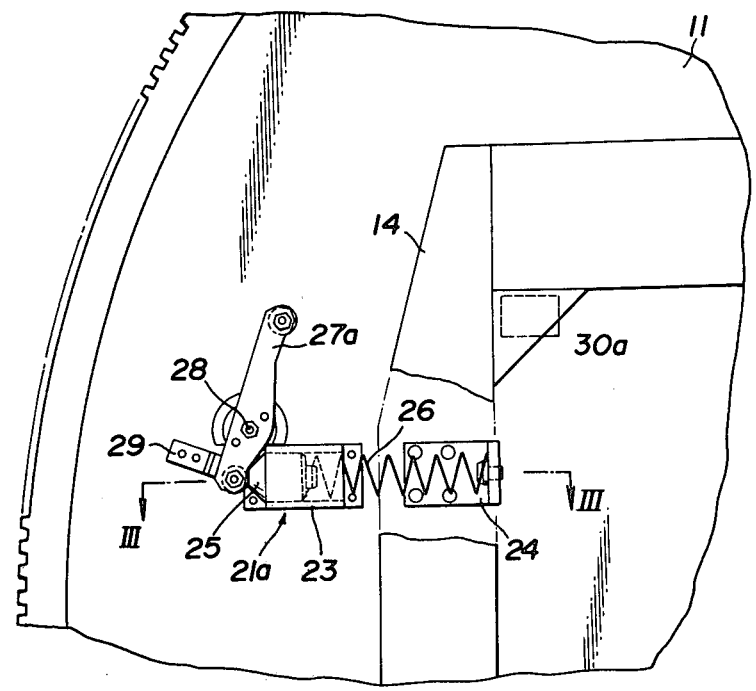
FIG. 2 is a diagrammatic front view, on an enlarged scale, showing one of the damper means of the scanning device of FIG. 1.
Figure 3:
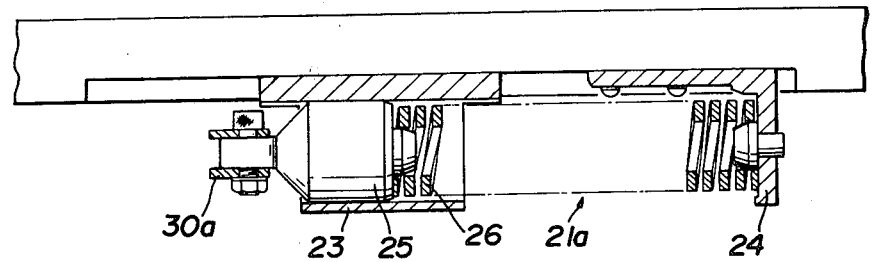
FIG. 3 is a diagrammatic sectional view, on an enlarged scale, of the damper means taken along the line III—III in FIG. 2.

A pedestal 10 is comprised of a welded assembly structure which is fabricated with shaped rigid members and plate members into a hollow box like frame configuration. A rotary disk 11 is provided in the form of a round disk, and it is mounted on rollers 12a and 12b which, in turn, are provided on the pedestal 10. A bore 13 for accommodation of a subject for examination therethrough is formed in the vicinity of the center of rotation of this rotary disk 11. A support 14 is engaged by guide rails 15, 15 provided on the rotary disk 11 so that the support 14 is able to make linear movements along these guide rails 15. An X-ray tube 16 and a detector 17 are installed on the support 14 so as to oppose each other. The X-ray tube 16 is provided with a collimator 18. Also, the detector 17 is equipped with a collimator 19. The X-ray emitting from the X-ray tube 16 is collimated into an X-ray beam of an angular divergence of, for example, 8° by these collimators. The detector 17 is equipped with a plurality of detecting elements which are arranged so as to cover this divergence of the X-ray.

The support 14 is caused to make linear movements by a barrel cam 20 which is provided on the rotary disk 11. This barrel cam 20 is arranged in a through-hole 11A which is formed in the rotary disk 11 and is supported on bearings 20A which, in turn, are fixed to this rotary disk 11. A cam groove of this barrel cam 20 is engaged by a pin 52 of an arm 51 which extends from the support 14, and this pin is supported on a bearing provided on the arm 51. Thus, by causing the barrel cam 20 to make one whole revolution by an electric motor of the rotary disk 11, the support 14 is caused to make reciprocating linear movements. As will be described later, the barrel cam 20 is arranged to be rotated at a first speed and also at a second speed which is greater than the first speed to thereby cause the support 14 to make reciprocating movements at two different speeds. The rotary disk 11 is rotated on the rollers 12a and 12b through a certain angle, for example 8°, for each forward movement or backward movement at each of the abovesaid two speeds.

In the scanning device according to the present invention, there are provided damper means for working upon the support 14, to insure that the support 14 is brought to a halt smoothly and that thereafter the support 14 will be able to quickly materialize its movement at a uniform speed, for each of its forward and backword movements.

This damper means has dampers 21a and 21b which are operated during the stage of movement of the support 14 at the first speed, and also has dampers 22a and 22b which are operated jointly with said dampers 21a and 21b, during the stage of movement of the support 14 at the second speed which is greater than the first speed.

Each of these dampers is comprised of such member that will not dissipate the energy which the damper has absorbed but will produce repelling action, i.e. a member whose repelling energy is not markedly smaller than its absorbed energy.

The dampers 21a and 21b each has a cylindrical member 23 and a U-shape member 24 which are fixed to the rotary disk 11. A slide 25 fits in the cylindrical member 23. A spring stopper is provided for the slide 25 and another stopper for the L-shape member 24. A compressible coil spring 26 is inserted between these spring stoppers. Arms 27a and 27b are mounted on the rotary disk 11 for pivotal movement about their shafts 28 and 28. A roller is provided at respective ends of these arms 27a and 27b. One of the rollers of each arm is in contact with a slide 25 with a slide 25, respectively. The arms 27a and 27b per se are brought into contact with the stoppers 29, 29 to be limited of the direction of rotation of these arms. The support 14 is provided with members 30a and 30b which are adapted to collide with the other rollers of the arms. As the support 14 is caused to make a linear movement in a certain direction, which may, for example, be toward the left side in FIG. 1 and as this movement progresses to an extent close to the end of the stroke of this movement, the member 30a acts to pivot this arm 27a counter-clockwise, causing the slide 25 to move within the cylindrical member 23 to thereby compress the coil spring 26 and to thus brake the support 14. As the direction of movement of the support 14 is changed, the support 14 will receive the repelling force of the coil spring 26. Thus, the support 14 will be caused to perform a movement at a uniform speed, after covering a short distance of acceleration, due to the driving force from the barrel cam 20 and also to the repelling force of the coil spring 26. As the support 14 is moved toward the right side in FIG. 1 and as it comes close to the end of its stroke, the support 14 is likewise subjected to a braking action and an accelerating action by the compression as well as the repelling forces of the coil spring 26 of the damper 21b via a member 30b provided on the support 14. The support 14, at each change into a forward movement or into a backward movement, is rapidly reduced of its speed of movement by the dampers, and thus this support 14 is urged to make accelerated movement in an opposite direction due to the driving force from the barrel cam 20 and also to the repelling force from the dampers.

The dampers 22a and 22b of another pair each has a cylinder 31 which is fixed to the rotary disk 11. Slides 32 and 33 are slidably arranged within each of these two cylinders 31. A coil spring 34 is inserted between the opposite faces of the two slides 32 and 33 within each cylinder 31. On the other hand, arms 35a and 35b are mounted on the rotary disk 11 for being rotatable about their corresponding shafts 35 and 36, respectively. The respective arms 35a and 35b are limited of their rotation to one direction by stoppers 35' and 35', respectively, which are provided on the rotary disk 11. These respective arms 35a and 35b are arranged on the rotary disk 11 in such way that, at each change of direction of movement of the support 14, both ends of these respective arms are brought into contact with members 39a and 39b which are provided on the support 14 or into contact with the slides 32 and 32 of the dampers 22a and 22b, depending on the direction of movement of the support 14, thus causing a compression of the coil springs 34 and 34 of these dampers alternately, and transmitting to the support 14 the repelling forces of these coil springs, alternately, depending on the direction of movement of the support 14.

A roller 40 is rotatably secured to the slide 32 of each of the dampers 22a and 22b. These rollers 40 are engaged by rotatable plates 42a and 42b, respectively, which, in turn, are supported by shafts 41 and 41 on the rotary disk 11. Rods 43 and 44 are coupled, at one end, to these rotatable plates 42a and 42b, respectively, through ball joints. The other end of the rod 44 is rotatably secured to a rotatable plate 46 which, in turn, is rotatably secured, by a ball joint, by a shaft 45 to the rotary disk 11. Furthermore, an end of a rod 47 is coupled to the rotatable plate 46 through a ball joint. The other end of this rod 47 is secured, jointly with the other end of the rod 43, to an arm 48 through a ball joint. This arm 48 is fixed to the rotary shaft of an electric motor 49.

Figure 4:
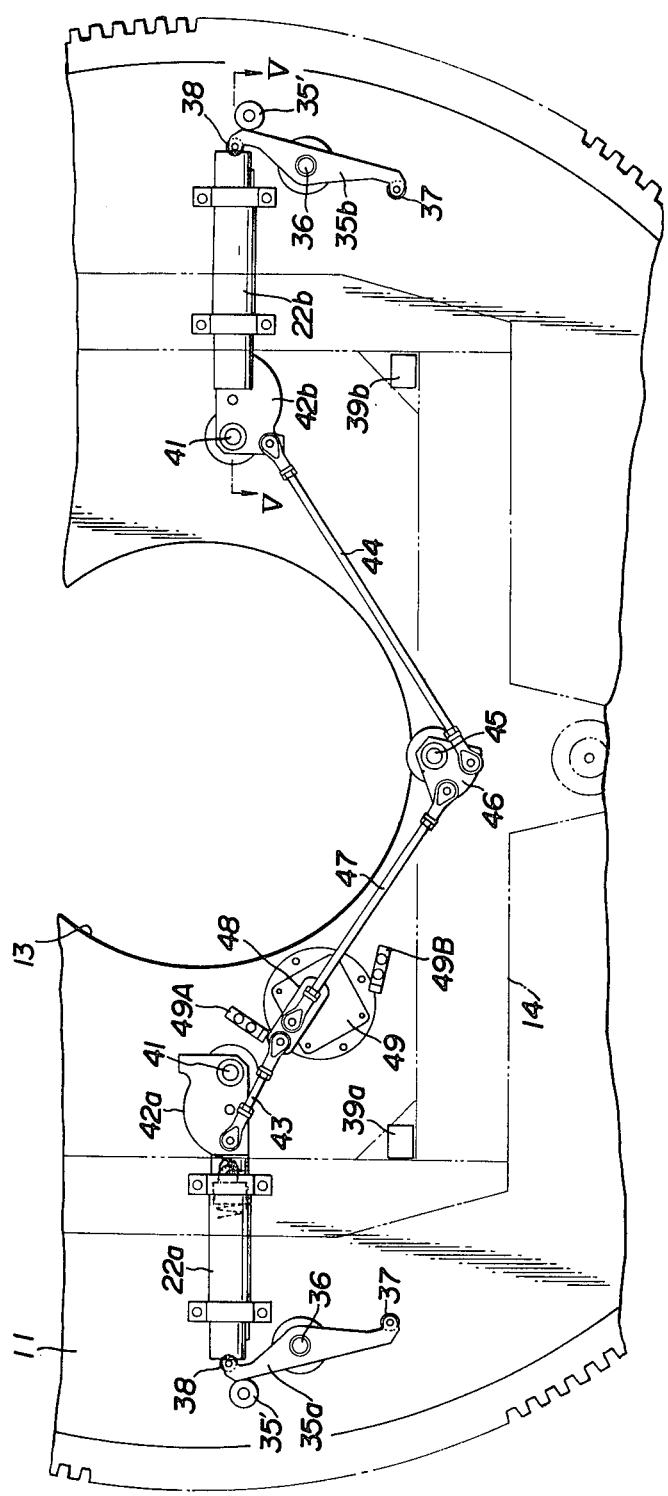
FIG. 4 is a diagrammatic front view, on an enlarged scale, showing another damper means in the scanning device mentioned above.
Figure 5:
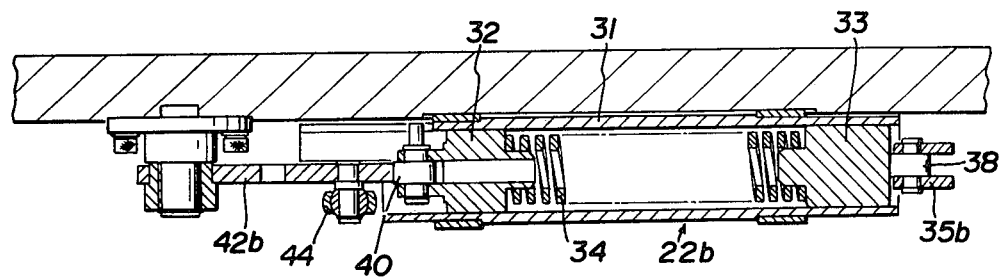
FIG. 5 is a diagrammatic sectional view, on an enlarged scale, of the damping means taken along the line V—V in FIG. 4.

This motor 49 is controlled so that, in each of the low-speed rotation and the high-speed rotation of the barrel cam 20, the rotary shaft of this motor is rotated in opposite directions, respectively. In FIG. 4, when the motor 49 rotates the arm 48 counter-clockwise, the rod 43 will be pulled downwardly, causing the rotatable plate 42a to rotate counter-clockwise, so that this rotatable plate will depart from the engagement with the slide 32 of the damper 22a. At the same time therewith, this rotation of the arm 48 causes the rod 47 to move so that the rotatable plate 46 will be caused to rotate counter-clockwise about the shaft 45. Whereby, the rod 44 will be moved to rotate the rotatable plate 42b counter-clockwise about the shaft 41, so that the rotatable plate 42b will depart from the slide 33 of the damper 22b. In this state, if the support 14 is moved at the first speed and if the arms 35a and 35b are rotated clockwise and counter-clockwise by the members 39a and 39b, respectively, the slides and the coil springs of the respective dampers will be moved jointly, and thus they will not display the damping and accelerating functions. However, the support 14 will be subjected sequentially to both the braking action first and then acceleration by the dampers 21a and 21b.

On the other hand, as the motor 49 rotates the arm 48 clockwise when the support 14 is moved at the second speed, the respective members mentioned above will be operated reversely of those operations stated above. Thus, the respective rotatable plates 42a and 42b will rotate up to the positions at which these rotatable plates are brought into contact with the rollers 40, 40 of the slides 32 of the respective dampers 22a and 22b, to thereby will move those respective slides to their required positions. In case, in this state, the support 14 is moved and in case the arms 35a and 35b are rotated in accordance with the direction of movement of the support 14, the slides 33 of the respective dampers 22a and 22b are moved accordingly. At such time, the other slides 32 are being prevented of their movement by their associated rotatable plates 42a and 42b. Therefore, the coil springs 34, 34 will become compressed in accordance with the movement of the slides 33, so that the support 14 will be reduced of its speed first and then will be accelerated of its speed. Accordingly, these dampers 22a and 22b, jointly with the dampers 21a and 21b, brake the support 14 immediately before the end of movement of the support in any one direction, and then they accelerate the speed of movement of this support at the time that this support sets out for movement in the opposite direction. Stoppers 50A and 50B are provided on the rotary disk 11 to determine the positions of maximum movements of the arm 48.

Figure 6:
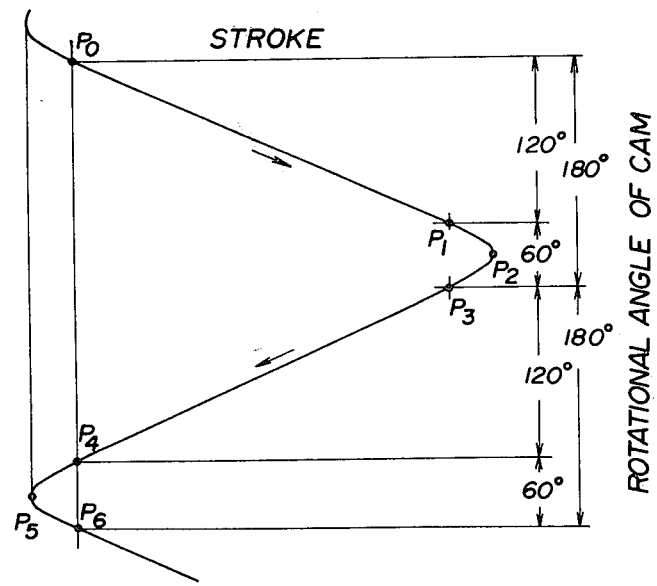
FIG. 6 is a cam diagram of the barrel cam which serves to drive the support in the scanning device of the present invention.

The barrel cam 20 has such cam groove as will cause the support 14 to make reciprocating movements as this barrel cam 20 makes one whole revolution. FIG. 6 shows the cam groove configuration of such barrel cam. Let us now assume that a pin 52 which is provided on the arm 51 of the support 14 is positioned at point $P_5$ of the cam groove. As the barrel cam 20 makes one half revolution, the pin 52 will move through a distance starting from $P_5$-$P_6(P_0)$-$P_1$-$P_2$, causing the support 14 to move in a certain direction. As this barrel cam 20 makes a further half revolution, the pin 52 will move from $P_2$-$P_3$-$P_4$-$P_5$, causing the support 14 to move in the opposite direction. The dampers accelerate the movement of the support 14 during the sections $P_5$-$P_6$ and $P_2$-$P_3$, and serve to reduce the speed of movement of this support during the sections $P_1$-$P_2$ and $P_5$-$P_6(P_0)$. That is, after the support 14 has been caused to make a movement at a uniform speed for the section $P_6(P_0)$-$P_1$ by the barrel cam 20, the movement speed of this support is reduced by the dampers during the section $P_1$-$P_2$. After the support has been brought to a halt at $P_2$, the support is subjected to acceleration of speed by the dampers in the section $P_2$-$P_3$, and the support is caused to make a movement in the opposite direction at a uniform speed during the section $P_3$-$P_4$. Again, the support is reduced of the speed of its movement in the section $P_4$-$P_5$ by the dampers. After the support has been brought to a halt at $P_5$, it is accelerated of its speed in section $P_5$-$P_6(P_0)$ by the dampers, and thereafter the support is caused to make a movement at a uniform speed.

Figure 7:
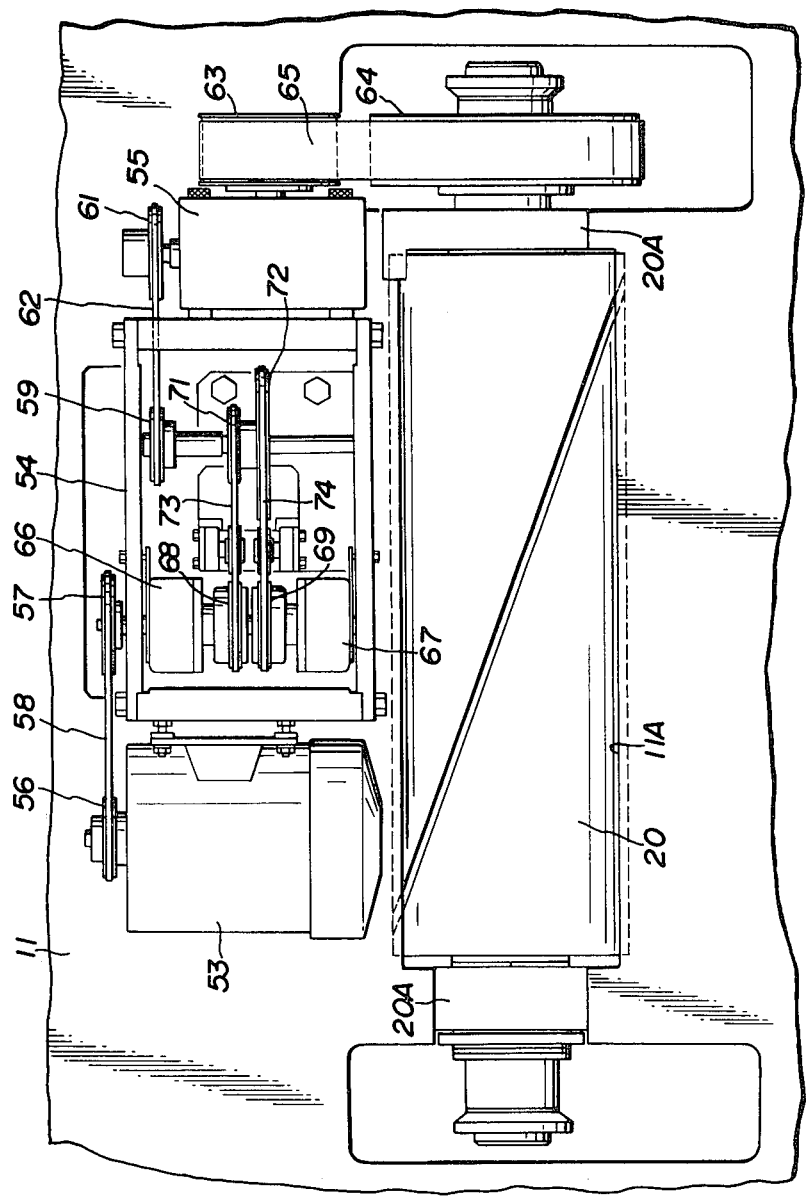
FIG. 7 is a diagrammatic rear view of a part of the scanning device, to show the driving mechanism of the barrel cam assigned to drive the support.

The driving of the barrel cam 20 is carried out by a driving mechanism provided on the rear side of the rotary disk 11. FIG. 7 shows the details of this mechanism. As stated above, the barrel cam 20 is arranged in the throughhole 11A which is formed through the rotary disk 11, and the shafts extending from the barrel cam 20 are supported on bearings 20A, 20A which, in turn, are fixed to the rotary disk 11. This driving mechanism is comprised of an electric motor 53, a speed-changing gear 54 and a speed-reducing gear 55. The motor 53 and the speed-reducing gear 55 are fixed to the speed-changing gear 54. This speed-changing gear 54 is fixed to the rear side of the rotary disk 11. The rotary shaft of the motor 53 is coupled to the input shaft of the speed-changing gear 54 by pulleys 56, 57 and a belt 58. The output shaft of the speed-changing gear 54 and the input shaft of the speed-reducing gear 55 are coupled to each other by pulleys 59, 61 and a belt 62. Also, the output shaft of the speed-reducing gear 55 is coupled to the barrel cam shaft by pulleys 63, 64 and a belt 65. The speed-changing gear 54 is provided with two solenoid (electromagnetic) clutches 66 and 67. Each of these clutches has a first member mounted on the input shaft of the speed-changing gear 54 via a bearing, a second member fixed to said input shaft, and a third member loosely receiving this second member. An electromagnet is mounted on said first member, and an armature is slidably attached to the third member. The second member which is magnetized by the electromagnet attracts the armature, so that the third member is adapted to be rotated jointly with the input shaft of the speed-changing gear 54 as an integral body. Pulleys 68 and 69 are fixed to the third member of such clutches as stated above. These respective solenoid clutches are controlled so that, while one of them is transmitting the rotation of the motor 53 to its mating pulley, the other one of the clutches disengages the connection between the motor and its mating pulley. The pulley 68 is coupled to a pulley 71 which is fixed to the output shaft of the speed-changing gear 54 via a belt 73. Similarly, the pulley 69 is coupled to a pulley 72 which is also fixed to said output shaft via a belt 74. The pulleys 68 and 69 have a same diameter. However, the pulley 71 has a diameter smaller than that of the pulley 72. When, thus, the clutch 66 is in its engaged state, the barrel cam 20 is rotated at a greater speed than it is rotated when the other clutch 67 is in its engaged state.

The rotary disk 11 is supported, at its circumference, on the rollers 12a and 12b, and both side peripheral surfaces of this disk 11 are supported on rollers 81a, 81a; 81b, 81b; and 81c, 81c. In this way, the rotary disk 11 is rotatably supported on the pedestal 10. The rotation of this rotary disk 11 is carried out by rotating, by an electric motor 83, a pinion gear 82 which is meshed with a toothed wheel 106 provided on the outer circumference of the rotary disk 11 and which is coaxial with the roller 12b. And, an intermittence transmission mechanism 84 which is comprised of, for example, known Geneva movement or mechanism transmits the rotation of the motor 83 to the pinion gear 82 in such way that, at each change of direction of movement of the support 14, the rotary disk 11 is rotated through an angle of 8° at a time.

As stated above, the rotary disk 11 is rotatably supported on a pair of rollers 12a and 12b which are provided on the pedestal 10 and also on three pairs of rollers 81a, 81a; 81b, 81b; and 81c, 81c. The rollers 12a and 12b are in contact with the outer circumference of the rotary disk 11, respectively. The roller 12a is fixed to a shaft 64 which is supported rotatably on a bearing which, in turn, is mounted on the pedestal 10. The roller 12b is rotatably supported on a fixed shaft provided on the pedestal 10. These rollers 12a and 12b support the whole weight of the rotary disk 11 carrying various members and also allow the rotation of this rotary disk. A solenoid or electromagnetic brake 89 is secured to the shaft to which is fixed the roller 12a, and is arranged so that, when the rotation of this roller is stopped, the rotary disk 11 is also stopped of its rotation due to the friction force at the contact face thereof with this roller 12a.

There are provided three pairs of rollers 81a, 81a; 81b, 81b; and 81c, 81c in order to limit the movement of the rotary disk 11 in the direction of the axis of its rotation. The rollers in each of these pairs are, in fact, are comprised of roller bearings, and they are arranged as a pair, sandwiching both side faces of the rotary disk 11 therebetween. Such paired rollers are provided in three pairs along the side peripheral surface of the circumference of the rotary disk 11. Each of the roller bearings is secured to a shaft 91 which is received partially in a boss which is fixed to the pedestal 10. Said shaft 91 is fixed to this boss by a small screw, so that the roller bearings are prevented from coming off their shafts 91. One of the shafts of each pair of rollers 81a, 81a; 81b, 81b; 81c, 81c is attached eccentrically to the boss, so that by rotating this shaft, the roller bearings are able to tightly engage both side faces of the rotary disk 11.

The rotation of the rotary disk 11 is effected by the electric motor 83 which is mounted on the pedestal 10. The rotation of this motor 83 is transmitted to the solenoid clutch 92 by a belt 95 which is applied between a pulley 93 secured to the output shaft of this motor 83 and a pulley 94 secured to one of the shaft ends of the solenoid clutch 92.

Figure 8:
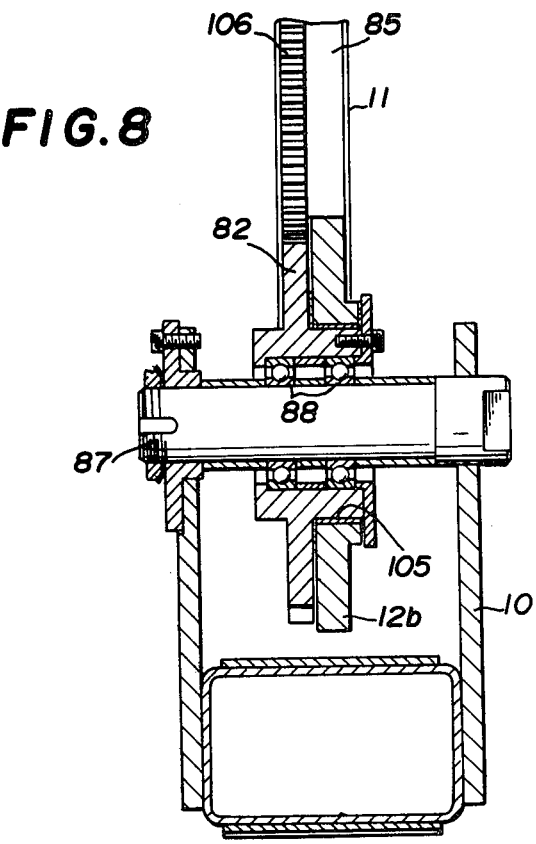
FIG. 8 is an enlarged sectional view of one of the rollers for supporting the rotary member, taken along the line VIII—VIII in FIG. 1.
Figure 9:
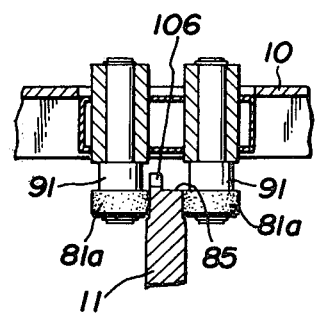
FIG. 9 is an enlarged sectional view of the other roller for supporting the rotary member, taken along the line IX—IX in FIG. 1.

This solenoid clutch 92 is equipped, at its output shaft, with a pulley 96 which, in turn, is connected via a belt 97 to a pulley 98 which is rotatably secured to the pedestal 10. A sprocket 99 is provided coaxially with the pulley 98. This sprocket 99 is connected via a chain 101 to a sprocket 102 which is provided on the input shaft of the intermittence transmission mechanism 84. A toothed wheel 103 is fixed to the output shaft of the Geneva movement 84. This toothed wheel 103 meshes with a gear 82. This gear 82 is provided coaxially with the roller 12b. As shown in FIG. 8, the pinion gear 82 is mounted on the shaft 87 which, in turn, is fixed to the pedestal 10. The roller 12b is coupled to the boss of the pinion gear 82 via a bearing 105. Because of this arrangement, the pinion gear 82 and the roller 12b are adapted to be able to rotate independently of each other.

On the other hand, teeth 10b are formed on the outer circumference of the rotary disk 11 to mesh with the pinion gear 82.

The diameters and the number of teeth of those pulleys, sprockets and toothed wheels as well the type of the Geneva mechanism which are stated above are selected to insure that the rotary disk 11 is brought to a halt either in the forward movement or in the backward movement of the support 14, and that the rotary disk 11 is caused to make limited revolutions through an angle of 8° at a time during the respective changes in the direction of movement of the support 14.

In the normal state of the device in which the solenoid clutch 92 is in its disengaged state, the solenoid brake 89 is in its operative state. When the motor 83 is started and when the solenoid clutch 92 is rendered to its engaged state, the rotation of this motor 83 is transmitted to the intermittence transmission mechanism 84, whereby the toothed wheel 103 of this intermittence transmission mechanism 84 rotates the pinion gear 82, so that the rotary disk 11 is rotated through an angle of 8°. Synchronization of this rotation of the rotary disk 11 with the movement of the support 14 is carried out by causing disengagement of the solenoid clutch 92 throughout the period in which the support 14 is making a movement at a uniform speed, and by causing engagement of the solenoid clutch 92 throughout the period in which the support 14 is being subjected to braking action and then to acceleration of speed of its movement. To ensure this synchronization, there is provided on the support, though not shown, a photo-detector carrying thereon a light source, and there is provided a plate, not shown, on the rotary disk 11, and there are provided, not shown, two small through-holes on this plate in association with the section to be covered by the support at a uniform speed. The engagement and disengagement actions of the solenoid clutch 92 is controlled by timing signals supplied from the photodetector. Alternatively, the controlling of the solenoid clutch 92 may be performed by both of the abovesaid timing signals and the signals generated from a detector which is provided in the support 14 of scanning devices in general to produce such timing signals that are generated for the purpose of re-construction of an image, whereby to make the synchronization to be performed in an all the more precise manner.

What is claimed is:

1. A scanning device for use in axial transverse tomographic apparatus, comprising, in combination:

a pedestal;

a rotary member rotatably supported on said pedestal;

means provided in said rotary member in the vicinity of center of rotation thereof for accommodating a subject for examination;

a support mounted on said rotary member for linear movement and supporting an X-ray source and its associated detector which are disposed on opposite sides of said accommodating means to face each other;

drive means for causing reciprocating movements of the support at a plurality of different speeds and for causing the rotary member to rotate through a certain angle at a time for each movement of the support in any one direction;

a plurality of damping means arranged on said rotary member so as to assume positions to work upon the support when said drive means causes the support to move at a plurality of different speeds, and having substantially great repelling forces enough to brake and accelerate this support at each changing of direction of movement thereof where said damping means comprises a first damper including a cylinder mounted on the rotary member, a member mounted on the rotary member at an end of said cylinder, a slide fit in said cylinder, and a coil spring provided between this slide and said member and being arranged on the rotary member to insure that the slide is moved at any changing of direction of movement of the support, and a second damper including a cylinder mounted on the rotary member, two slides fit in this cylinder, and a coil spring inserted between these two slides, and being arranged on said rotary member to insure that one of these two slides is moved at any changing of direction of movement of said support; and change-over means for selectively rendering a part of said damping means to a state of working upon the support and to an inoperative state for the support in accordance with the speed of movement of this support where said change-over means acts to allow free movement of the other one of said two slides of the second damper and also to lock this other slide in accordance with a speed of movement of the support.

2. A scanning device according to claim 1, in which:

said change-over means comprises:

two members provided on said rotary member for rotation between a position at which these members are brought into contact with said other slide of said second damper and a position at which these members depart from this other slide;

an electric motor provided on the rotary member; and a linkage mechanism provided between said electric motor and said two members to rotate these members to a same said position at the same time.

3. A scanning device according to claim 2, in which:

said linkage mechanism includes:

an arm fixed to a rotation shaft of an electric motor;

a first rod connecting one of said two members to said arm to allow this member to rotate in accordance with a rotation of said arm;

a rotatable plate provided on the rotary member;

a second rod connecting said arm to said rotatable plate to allow this rotatable plate to rotate; and a third rod connecting said rotatable plate to said other member to allow this other member to rotate in accordance with a rotation of said rotatable plate.

4. A scanning device according to claim 3, further comprising means rotatably provided on said rotary member for causing said movement of the slides of the damping means at any changing of direction of the support, said means including an arm having one end adapted to be brought into contact with said support and having the other end adapted to be brought into contact with said slides at said changing of direction of movement of the support.

* * * * *